United States Patent [19]

Rudy et al.

[11] Patent Number: 4,897,258

[45] Date of Patent: Jan. 30, 1990

[54] PERIODONTAL COMPOSITION AND METHOD

[75] Inventors: Jerome B. Rudy; Melvin Denholtz, both of Livingston; Jeffrey R. Denholtz, Stanhope; Peter D. Bohm, Freehold, all of N.J.

[73] Assignee: Peroxydent Group, Livingston, N.J.

[21] Appl. No.: 149,402

[22] Filed: Jan. 28, 1988

Related U.S. Application Data

[63] Continuation-in-part of Ser. No. 2,177, Jan. 12, 1987, Pat. No. 4,837,008, and a continuation-in-part of Ser. No. 721,210, Apr. 9, 1985, and a continuation-in-part of Ser. No. 532,182, Sep. 14, 1983, abandoned.

[51] Int. Cl.$^4$ .................. A61K 7/20; A61K 33/40
[52] U.S. Cl. ........................ 424/53; 424/613
[58] Field of Search ............ 424/49, 53, 130, 57, 424/613

[56] References Cited

U.S. PATENT DOCUMENTS

| | | | |
|---|---|---|---|
| 959,605 | 5/1910 | Queisser | 424/53 |
| 1,018,240 | 2/1912 | Von Foregger | 424/53 |
| 1,863,116 | 6/1932 | Heymann | 424/53 |
| 2,052,694 | 9/1936 | Breivogel | 424/53 |
| 2,054,742 | 9/1936 | Elbel | 424/53 |
| 2,090,437 | 8/1937 | Woldman | 424/53 |
| 2,501,145 | 3/1947 | Smith | 424/53 |
| 3,250,680 | 5/1966 | Menkart et al. | 424/56 |
| 3,574,824 | 4/1971 | Echeandia et al. | 424/50 |
| 3,703,578 | 11/1972 | Cella et al. | 424/49 |
| 4,132,771 | 1/1979 | Schreiber et al. | 424/49 |
| 4,159,316 | 6/1979 | Januszewski et al. | 424/49 |
| 4,187,287 | 2/1980 | Schreiber et al. | 424/49 |
| 4,311,528 | 1/1982 | Dietz et al. | 433/228.1 |
| 4,405,599 | 9/1983 | Smigel | 424/53 |
| 4,487,757 | 12/1984 | Kiozpeoplou | 424/7.1 |
| 4,522,805 | 6/1985 | Gordon | 424/49 |
| 4,528,180 | 7/1985 | Schaeffer | 424/52 |
| 4,537,764 | 8/1985 | Pellico et al. | 424/49 |
| 4,582,701 | 4/1986 | Piechota | 424/49 |
| 4,603,045 | 7/1986 | Smigel | 424/52 |
| 4,627,972 | 12/1986 | Gioffre et al. | 424/52 |
| 4,647,451 | 3/1987 | Piechota | 424/52 |
| 4,687,663 | 8/1987 | Schaeffer | 424/52 |
| 4,788,052 | 11/1988 | Ng et al. | 424/53 |
| 4,837,008 | 6/1989 | Rudy et al. | 424/53 |

FOREIGN PATENT DOCUMENTS

| | | |
|---|---|---|
| 2513119 | 3/1983 | France . |
| 336017 | 4/1972 | U.S.S.R. . |
| 336018 | 4/1972 | U.S.S.R. . |

OTHER PUBLICATIONS

Bernard et al. GA, 99: 10899h of FR. 2513119, Mar. 25, 1983.
Smigel, GA, 99: 200363b of U.S. Pat. No. 4,405,599, Sep. 20, 1983.
Smigel, GA, 105: 120546r of U.S. Pat. No. 4,603,045, Jul. 24, 1986.
Gruhn, I. et al., Stomatol D.D.R. 28(8): 569–575, Aug. 5, 1978.
Klinger, G. et al., Stomatol D.D.R. 25(12): 801–808, Dec. 8, 1975.
Volnov et al., GA, 77: 52373h of U.S.S.R. 336017, Apr. 21, 1972.

*Primary Examiner*—Shep K. Rose
*Attorney, Agent, or Firm*—Klauber & Jackson

[57] ABSTRACT

A non-aqueous paste or gel dentifrice composition comprising a water soluble, non-aqueous vehicle having dispersed therein an orally acceptable inorganic peroxide and a bicarbonate salt. The quantities and relative proportions of the peroxide and bicarbonate are sufficient to provide quantities of bactericidally active oxygen upon breakdown of said peroxide when intermixing with water and introduction into the oral cavity. The bicarbonate also provides a neutral or basic pH upon dispersal and substantial dissolution of the composition in water. Preferably the composition comprises sodium bicarbonate and calcium peroxide in a preferable weight ratio (based on 60% $CaO_2$ in the peroxide) of from about 4:1 to 6:1.

8 Claims, No Drawings

PERIODONTAL COMPOSITION AND METHOD

RELATED APPLICATION

This application is a continuation-in-part of U.S. applications Ser. Nos. 002,177, filed Jan. 12, 1987, and of 721,210, filed Apr. 9, 1985, and of 532,182, filed Sept. 14, 1983, now abandoned.

BACKGROUND OF INVENTION

This invention relates generally to periodontal compositions and methods; and relates more specifically to compositions and methods of this type which are capable of providing active oxygen in the oral cavity, to thereby inhibit the motility of harmful oral bacteria.

Recent developments in dental technology, coupled with topical fluorides, sealants and fluoridization of municipal water supplies, have fostered a remarkable decrease in tooth decay. While laymen have associated decay with the main cause of tooth loss, it is well-known to dental experts that the major cause of tooth loss after the age of 35, is in fact gum disease. Indeed, gum disease has now reached epidemic proportions — over 90% of the general population are considered by most such experts to suffer from some form of gum disease.

Since gum disease is not painful, it is easily undetected, and in consequence, untreated. Without the acute pain associated with a toothache, most people indeed pay little or no attention to their gums until the disease has reached an advanced stage and they are threatened by the loss of teeth.

Recent studies and investigations, however, have conclusively demonstrated that the major cause of gum disease is specific bacteria that live and thrive in the gum crevices. These bacteria give off toxins that attack the bone, cementum and gums which support the teeth. If one is able to eliminate the cause (bacteria), the result is healing of the gums.

Dentists and periodontists have long known that certain substances can exert powerful cleansing and sanitizing action on the teeth, the gums and the oral cavity. Hydrogen peroxide, baking soda (sodium bicarbonate), and salt (sodium chloride) are examples of such materials. The major recent proponent of an antimicrobial method based on such knowledge, is Dr. Paul Keyes; and indeed this new therapy is now widely recognized as the "Keyes Technique".

Prior to the popularization of Dr. Keyes methodology most periodontal cases were referred to periodontists, and the method of treatment was often surgery (gingivectomy). This surgery is expensive and painful. Because of the pain, suffering, and expense associated with gum surgery, a rapidly growing number of dentists are, however, now adopting the concept of Dr. Keyes and his non-surgical approach to gum disease.

Instead of a scalpel, Keyes relies on such ordinary household items as salt, hydrogen peroxide and baking soda to create a hostile climate for these troublesome bacteria. The baking soda neutralizes the acidic toxins given off by the bacteria, and the peroxide effectively kills the anerobic bacteria that cause gum disease. The anerobic bacteria cannot survive in an oxygenated environment.

Unfortunately baking soda and peroxide must be mixed daily, because these two elements decompose rapidly when mixed together. This is a messy, time-consuming and unpleasant daily chore. As a result, it is very difficult for the potential beneficiaries of such therapy to faithfully adhere to the regimen.

The Keyes method is e.g. described in an article by Judith E. Randal in A. H. (March/April 1982), at pages 82–85, and elsewhere. According to the procedure, once a day a patient is required to perform the following routine:

(a) Two tablespoons or so of baking soda are wet with enough hydrogen peroxide to form a thick paste;

(b) A rubber tip, of the kind found on some toothbrush handles, is employed to massage the paste into the spaces between the teeth and at the gum margins on both the front and back sides of the teeth;

(c) Again using the paste, the patient massages the gums and gum margins front and back with an electric toothbrush or a child-sized manual toothbrush;

(d) Enough salt is added to a glass of warm water so that some remains in the bottom even when the solution is stirred;

(e) The liquid part of the mixture is poured into a Water Pik ®; and with the device set at moderate speed, the teeth and gums, front and back are rinsed; and (f) A glass of plain water is run through the Water Pik ® to prevent salt damage to its internal parts.

As is readily apparent from the above description of the Keyes method, it is a relatively complex and burdensome procedure for an individual patient to employ on a daily basis. It would clearly be desirable for a patient to be able to perform the Keyes method or a method similarly effective in an easier manner, e.g., with a single composition.

However, merely combining the components employed by Keyes into a "prepackaged" formula will not provide an effective means for accomplishing the desired results. Specifically, the hydrogen peroxide and/or sodium bicarbonate can in a combination decompose rapidly. Hydrogen peroxide (or other peroxide) can break down in the presence of alkalinity, heat, light and/or metal ions as follows:

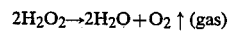

Similarly, sodium bicarbonate can break down in the presence of hydrogen peroxide, heat and/or water as follows:

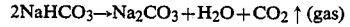

Since the active materials are lost or diminished, such a formula will have a short shelf life. Moreover, the gas evolution is especially undesirable with a tooth paste or gel, since such gas evolution can cause swelling and/or bursting of tubes or other packages containing same. All of these factors are undesirable for a consumer product.

SUMMARY OF INVENTION

Now in accordance with the present invention, a periodontal composition is provided, which includes a peroxide and a bicarbonate, in a single highly stable form, which is therefore susceptible to conventional modern packaging and dispensing systems, and which can be readily and effectively used by the consumer.

The composition can be prepared as a non-aqueous paste or gel dentifrice, and generally comprises a water soluble, nonaqueous vehicle having dispersed therein an orally acceptable inorganic peroxide and a bicarbonate salt. The composition is substantially anhydrous, and the amounts and relative proportions of the peroxide and bicarbonate are sufficient to provide a level of bactericidally active oxygen upon breakdown of the peroxide by tissue contact and by reaction with the bicarbonate in the oral cavity of the user. The amount of the bicarbonate is effective to provide a neutral or basic pH upon dissolution of the composition in water. The composition may be contacted with water in mouth saliva, a moistened toothbrush, or by contact with water from an oral irrigating device such as a Water-Pik®. Also the composition can be directly disolved in a volume of water to provide a mouth wash.

In our aforementioned U.S. Pat. No. 4,837,008, now at least one of the peroxide or bicarbonate is provided with a water-soluble barrier coating, which is, however, insoluble in the non-aqueous vehicle, to prevent reaction therebetween in the absence of water dissolution of the coating. All of the components of the composition are water soluble, whereby upon the composition being contacted with substantial quantities of water, including in the oral cavity of a user, dissolution of the barrier coating enables reaction of the peroxide and bicarbonate to augment release of active oxygen, to inhibit the motility of oral bacteria in said cavity. Dissolution of the bicarbonate further, enables neutralizing of acid secretions in the oral cavity.

In accordance with the present invention, it has unexpectedly been found, that a periodontal composition including a peroxide and bicarbonate may be prepared in a single highly stable form which has all of the advantages of the compositions disclosed in our aforementioned patent applications, and which does not require a barrier coating.

More specifically the compositions of the present invention are based upon a combination of calcium peroxide and sodium bicarbonate, wherein the weight ratios of bicarbonate to peroxide are in the range of 4:1 to 8:1, and preferably in the range of 4:1 to 6:1 (where the expressed quantity of peroxide is 60% $CaO_2$). Where combinations as set forth are provided, the compositions can be readily stored in conventional dispensing containers, e.g., "toothpaste tubes" or the like, for sustained periods without perceptible instability — as would, e.g., cause swelling of the packages. Even after such sustained storage the compositions when admixed with water, produce abundant oxygen to enable its use as an effective periodontal agent.

While we are aware of Mayer, U.S. Patent No. 3,251,780 which discloses a composition including calcium peroxide and sodium bicarbonate, such disclosure is directed at a dry powder for use in the bleaching of wood pulp and textiles, and has no relation to dentifrice gels or pastes. Mayer's powder indeed provides a pH of from about 9.60 to 12.13, and has a weight ratio of from about 1.5 to about 3.4 parts sodium bicarbonate to each part of calcium peroxide, which characteristics are very distinct from those of the present invention.

Although not normally necessary, the compositions of the invention may also include one or more auxiliary stabilizers, which serve to further reduce the possibility of premature decomposition of the peroxide, or of premature reaction between peroxide and bicarbonate components. These can comprise e.g. dessicants which remove or absorb any trace water which may find its way into the compositions. A preferred material for these purposes is colloidal pyrogenic silica, which also serves in the composition as a thickener.

The compositions may also include small amounts of normal dentifrice adjuvants, such as flavoring agents (typically 0.1 to 5%); cleansing and foaming agents (surfactants), typically as 0.1 to 10%; normally acceptable dental abrasives or polishing agents (preferably 1 to 15%, although higher amounts can be used), such as dicalcium phosphate, suitable calcined kaolins, etc.; sweetening agents, colorants and the like.

The compositions may also include fluorine-containing compounds as are known for use in the dentifrice art, such as sodium fluoride, sodium monofluorophosphate, stannous fluoride, and the like.

DETAILED DESCRIPTION OF INVENTION

The peroxide component of the compositions of the invention preferably comprises calcium peroxide, which is readily available from several commercial sources — e.g., the FMC grade which is 60% pure $CaO_2$.

The peroxide component of the compositions of the invention is included in an amount sufficient to allow release of sufficient oxygen when the composition is contacted with water, e.g. during brushing of teeth, to inhibit the motility of oral bacteria, e.g., in the treatment of gingivitis. Typically, the peroxide can be employed in the composition of the present invention in amounts so that at least about 1% of the composition comprises a peroxide. Preferably, the peroxide comprises from about 1 to about 10% by weight of the composition. More preferably, the peroxide comprises from about 4 to about 6% by weight of the composition. A typical calcium peroxide concentration in the composition is about 4 to 5% by weight. (In all instances herein the percentages of calcium peroxide are based upon a commercial grade including 60% $Ca_2$).

The bicarbonate salts employed in the composition of the invention include any which are sufficiently soluble so that, when the composition is contacted with water, e.g., in the brushing of teeth, a neutral or basic pH is provided by the bicarbonate. Suitable bicarbonates include alkali metal and alkaline earth metal bicarbonates. Examples of suitable bicarbonates include sodium bicarbonate, potassium bicarbonate, lithium bicarbonate, calcium bicarbonate, magnesium bicarbonate, and the like or mixtures thereof. A preferred bicarbonate is sodium bicarbonate. If it is desirable, e.g., with a patient having high blood pressure, etc., sodium-free compositions or low sodium compositions can be employed, such as potassium bicarbonate or magnesium bicarbonate. Combinations of bicarbonate salts can also be employed, e.g. sodium and potassium bicarbonates.

The bicarbonate is included in the composition of the invention in an amount sufficient to provide a neutral and basic pH when the composition is contacted with water, (as is in the oral cavity), preferably a pH of from about 7.0 to about 9.5. The amount of bicarbonate actually employed in the method of the invention can vary greatly depending upon the form of the composition and its intended method of application. This is subject to the weight ratio as between the bicarbonate and the calcium peroxide, which is critical to assuring release of the peroxygen content while yet providing stability to the present compositions. Where the preferred sodium bicarbonate is used, the said ratio of bicarbonate to calcium peroxide should be in the range of 4:1 to 8:1, and preferably is in the range of 4:1 to 6:1.

In a further aspect of the invention, it has been found that by increasing the particle size of the bicarbonate salt, which decreases its surface area, the stability of the peroxide in the compositions of the invention is increased. For example, as among grade numbers 1, 2 and 5 baking soda available from Allied Chemical (Bulletin No. 513-016 U.S.A.), the No. 5 grade provides the greatest peroxide stability in the composition of the invention, while the No. 2 grade provides almost the same stability. Preferably, the particle size of the bicarbonate salt is such that it provides a residual peroxide level of from about 95 to about 99%, more preferably, from about 97.5 to about 99%, when the composition is stored in a closed container at room temperature for about 6 weeks. Typical screen analysis of such grades of baking soda are set forth below:

| Screen Analysis | GRADE BAKING SODA | | |
|---|---|---|---|
| | No. 1 | No. 2 | No. 5 |
| Cumulative % on | | | |
| U.S. No. 60 | | | 1 |
| 80 | | trace | 37 |
| 100 | 1 | 1 | 72 |
| 170 | 25 | 68 | 98 |
| 200 | 38 | 89 | 100 |
| 325 | 71 | 99 | |
| Bulk Density (lb/ft$^3$) | 53 | 55 | 46 |

Preferably, the bicarbonate employed in the composition of the present invention has an average particle size of from about 100 to about 2,000 microns, more preferably from about 200 to about 800 microns. The surface area of the bicarbonate particles in the composition of the invention can be further reduced by agglomerating the particles to form aggregates with less surface area than the component particles.

The hydrophilic, non-aqueous vehicles employed in the tooth paste or gel composition of the present invention are water soluble so that they facilitate the action of the bicarbonate and peroxide during brushing with the composition. Thus, the vehicles employed in the present invention preferably rapidly dissolve with water when used by a consumer, e.g., in mouth rinse water or the water in a pre-moistened toothbrush in saliva, or in the post-brushing water rinse. The active species, i.e., the peroxide and bicarbonate salt, may be dispersed, or suspended in the vehicle.

Suitable hydrophilic, non-aqueous vehicles for use in the present invention include polyalkylene glycols, non-ionic surfactants, anionic surfactants, ampholytic surfactants, cationic surfactants and alkanolamides. Also suitable are glycerol, propylene glycol or sorbitol in combination with silica, clay, polymer and/or gum thickeners, and perhaps dicalcium phosphate as a cleansing agent.

The hydrophilic, non-aqueous vehicles preferably provide a viscosity for the composition suitable for its use as a toothpaste or gel, e.g. between about 2,000 cps. to about 200,000 cps. If the selected vehicle does not itself provide the desired viscosity, viscosity modifiers, such as barrier coated dicalcium phosphate, finely divided pyrogenic silica and the like may be added, and/or other known and orally acceptable vehicle agents can be included to provide such desired viscosity.

Typically, the hydrophilic, non-aqueous vehicles employed in the tooth paste or gel compositions of the invention are present in an amount of from about 45 to about 90% by weight.

Suitable polyalkylene glycols for use as vehicles in the present composition include those having molecular weights of from about 200 to about 20,000. Such materials range in physical state from thin liquids to pastes to solids with increasing molecular weight.

Preferred polyalkylene glycols for use as vehicles in the present invention are polyethylene glycols having the general formula H(OCH$_2$CH$_2$)nOH, where n is greater than or equal to 4. These liquid and solid polymers are widely known and available under trademarks such as Carbowax ® (Union Carbide). In general, each polyethylene glycol (PEG) is identified by the manufacturer by a number which corresponds to its average molecular weight, e.g. "Carbowax ® 400". Preferred PEG's for use in the present invention have a molecular weight in the range of from about 400 to about 8,000. Mixtures of such polyethylene glycols of differing molecular weights (and for that matter other vehicles discussed herein) can be employed to provide desirable viscosity characteristics for the composition.

Other suitable polyalkylene glycol vehicles include materials of the formula

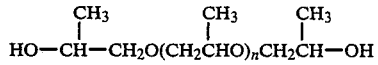

or

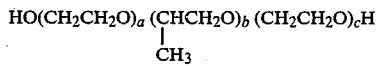

wherein n, a, b and c are integers such that the molecular weights of such materials are in the range of from about 1,100 to about 14,000. Also sutiable are the polyoxyalkylene derivatives of ethylene diamine, e.g., the materials sold under the trademark TETRONIC.

Suitable non-ionic surfactants for use as the hydrophilic, non-aqueous vehicle in the tooth paste or gel composition of the invention include materials such as polyoxyethylene sorbitan fatty acid esters, e.g., materials sold under the trademark TWEEN. Examples of such materials are polyoxyethylene (20) sorbitan monolaurate (TWEEN 20), polyoxyethylene (20) sorbitan monopalmitate (TWEEN 40), polyoxyethylene (20) sorbitan monostearate (TWEEN 60), polyoxyethylene (4) sorbitan monostearate (TWEEN 61), polyoxyethylene (20) sorbitan tristerate (TWEEN 65), polyoxyethylene (20) sorbitan monooleate (TWEEN 80), polyoxyethylene (5) Sorbitan monooleate (TWEEN 81), and polyoxyethylene (20) sorbitan trioleate (TWEEN 85).

Polyoxyethylene fatty acid esters are also suitable for use as the vehicle in the tooth paste composition of the invention. Examples include those materials sold under the trademark MYRJ such as polyoxyethylene (8) stearate (MYRJ 45) and polyoxyethylene (40) stearate (MYRJ 52).

Another suitable class of non-ionic surfactants for use in the vehicle in the present invention are polyoxyethylene fatty ethers, e.g., the materials sold under the trademark BRIJ. Examples of such materials are polyoxyethylene (4) lauryl ether (BRIJ 30), polyoxyethylene (23)

lauryl ether (BRIJ 35), polyoxyethylene (2) cetyl ether (BRIJ 52), polyoxyethylene (10) cetyl ether (BRIJ 56), polyoxyethylene (20) cetyl ether (BRIJ 58), polyoxyethylene (2) stearyl ether (BRIJ 72), polyoxyethylene (10) stearyl ether (BRIJ 76), polyoxyethylene (20) stearyl ether (BRIJ 78), polyoxyethylne (2) oleyl ether (BRIJ 93), polyoxyethylene (10) oleyl ether, and polyoxyethylene (20) oleyl ether (BRIJ 99).

In one embodiment of the invention, a portion of a non-ionic surfactant employed in the vehicle in the composition of the invention can be substituted with a lipophilic surfactant, e.g., sorbitan fatty acid esters such as the materials sold under the trademark ARLACEL. Suitable lipophilic surfactants include sorbitan monolaurate (ARLACEL 20), sorbitan monopalmitate (ARLACEL 40), sorbitan monostearate (ARLACEL 60), sorbitan monooleate (ARLACEL 80), sorbitan sesquioleate (ARLACEL 83), and sorbitan trioleate (ARLACEL 85). Typically, from about 10 to about 90% of the non-ionic surfactant can be substituted by a lipophilic surfactant, preferably from about 25 to about 50%.

As noted above, other classes of surfactants such as cationic surfactants, anionic surfactants, ampholytic surfactants and alkanolamides can also be employed as the vehicle in the composition of the present invention. Such materials can be employed either by themselves as the vehicle or together with a polyakylene glycol or a non-ionic vehicle as discussed above. Examples of suitable anionic, cationic, ampholytic and alkamolamide surfactants include di-tallow dimethyl ammonium chloride, sodium lauryl sulfate, the material

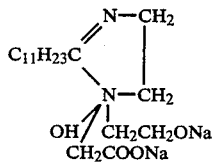

sold under the trademark MIRANOL, and coconut alkanolamide. Typically, when these materials are used as part of the vehicle, they are substituted for from about 10 to about 90% by weight, preferably from about 25 to about 50% by weight, of the main vehicle used in the composition, e.g., a polyalkalene glycol or a non-ionic surfactant as discussed above.

Auxiliary stabilizers can also be included in the compositions of the invention in order to augment stabilization of the bicarbonate, and especially of the peroxide component. These can comprise dessicating agents to absorb trace water, or can comprise chemical stabilizers.

Any orally acceptable material that stabilizes the peroxide during storage of the composition in a closed container can e.g. be employed as an auxiliary stabilizer in the present composition. Examples of suitable such stabilizing agents include desicating agents, sequestering agents, colloidal particles, free radical preventatives, inorganic hardness salts, acidulating agents, and mixtures of such stabilizing agents.

Examples of suitable dessicating agents include magnesium sulfate, sodium sulfate, calcium sulfate, calcium chloride and colloidal silica, e.g., colloidal silica particles sintered together in chainlike formations having surface areas of from about 50 to about 400 square meters per gram such as materials sold under the trademark Cab-O-Sil ® by Cabot Corp. It is believed that such materials act to stabilize the compositions of the invention by, for example, absorbing any existing water either present in or contacted with the composition so as to further preclude breakdown of the peroxide and/or bicarbonate.

Colloidal pyrogenic silica serves a further purpose in the present compositions, i.e. it is a well-recognized thickener, and is very useful in achieving a desired consistency for both practical and aesthetic reasons.

Examples of suitable sequestering and/or chelating agents include ethylene diamine tetraacetic acid (EDTA) or its sodium salts, nitrilotriacetic acid or its sodium salts, diethylene triamine pentaacetic acid (DPTA), or DEQUEST phosphonates available from Monsanto. It is believed that such chelating or sequestering agents stabilize the compositions of the invention, for example, by tying up metal ions such as $Fe^{+3}$, $Mn^{+2}$, $Cu^{+2}$, etc. that can catalyze the decomposition of peroxide in the compositions.

Other effective auxiliary stabilizers for use in the present composition include in addition to the colloidal particles such as the pyrogenic silica mentioned above, finely divided clays, zeolites and insoluble metallic oxides, e.g., magnesium and aluminum oxide. The pyrogenic silica materials are a preferred auxiliary stabilizing agent in the compositions of the present invention.

Also, free radical inhibitors or preventatives such as butyl hydroxytoluene, butyl hydroxyanisole and beta carotene can also reduce the instability of peroxide in the composition of the invention.

Inorganic hardness salts such as calcium or magnesium inorganic compounds also reduce peroxide instability. Examples of such compounds include magnesium carbonate, magnesium chloride, calcium sulfate, calcium chloride and the like.

The addition of anhydrous acidulating agents or their salts (powdered or granulated), also provide improvement in peroxide stability in the compositions of the invention. Examples of suitable acidulating agents for use in the present invention include ascorbic acid, tartaric acid, phosphoric acid as well as the chloride, sulfate or nitrate salts of calcium, magnesium or ammonium.

The inclusion of an auxiliary stabilizing agent in the composition of the present invention has been found to provide increased stability of the compositions in comparison to compositions without such stabilizing agent. Typically, the auxiliary stabilizing material is included in the compositions of the present invention in an amount of from 0.1 to about 7.5%, preferably from about 1 to about 5%. For example, when pyrogenic colloidal silica materials are used as an auxiliary stabilizing agent (and thickener), suitable amounts thereof are from 1 to about 7.5% by weight, preferably from about 3 to about 5% by weight.

One embodiment of the invention and composition also includes chloride and/or sulfate salts such as alkali metal chlorides or sulfates, alkaline earth metal chlorides or sulfates, or mixtures thereof. Suitable chloride salts for use in the composition of the invention include sodium chloride, potassium chloride, lithium chloride, calcium chloride, magnesium chloride, sodium sulfate, potassium sulfate, magnesium sulfate, etc.

Typically, the chloride salts or other salts are included in the composition of the present invention in amounts of from about 1 to about 50% by weight of the composition. Preferably, the chloride or other salts are included in an amount of from about 1 to about 15% by weight of the composition.

The compositions of the invention can include many other components which are conventional in the art, again depending upon the ultimate use to be made of the composition. As with all the components of the composition, these components should preferably be of the class generally recognized as safe, especially for use in the mouth. For example, the composition of the invention can include conventional adjuvants, e.g., colorants, flavors, sanitizing agents, dentally acceptable abrasives, cleansing agents, and the like.

The compositions of the present invention can be prepared by methodology conventional in the art. For example, the peroxide material can be physically mixed with the bicarbonate salt, and any other materials to be included in the compositions of the invention, such as a chloride salt or other carriers and/or adjuvants. The composition can be prepared into a paste or gel again in a manner conventional for preparing such paste or gels as is well known in the art by merely including the desired amount of the peroxide, auxiliary stabilizer (if used) and bicarbonate in the desired hydrophilic, non-aqueous vehicle. As noted above, the paste or gel is non-aqueous.

In a preferred method of preparing a composition of the present invention, an auxiliary stabilizer and thickener (where used) such as a pyrogenic colloidal silica material, is first mixed with the hydrophlic, non-aqueous vehicle, such as polyalkylene glycol, e.g. of polyethylene glycols such as Carbowax ® 400 and Carbowax ® 8,000. Additonal surfactants can also be present to provide good foaming when used in the mouth. To such mixture is added the peroxide with stirring. The bicarbonate salt is then added to the mixture containing the peroxide. Other desired adjuvants can be added at the tail end of this process.

The compositions of the present invention as noted above can be used to treat periodontal disease. In such treatment, it is believed that the composition of the invention attacks the anerobic bacteria that cause such periodontal disease. In the method of the present invention, the compositions described above are applied to the gums of the patient, e.g., a mammal such as man, in an amount effective to inhibit the bacterial motility of the oral anerobic bacteria and other bacterial types.

The invention is further illustrated by the following Examples, which are, however, intended to be illustrative, and not delimitive of the invention which is otherwise set forth:

Example I

A composition in accordance with the present invention was prepared in the form of a paste or gel. A high molecular weight polyethylene glycol, Carbowax ® 8,000, was warmed and combined with a low molecular weight polyethylene glycol, Carbowax ® 400. Baking soda is added with stirring. A foaming agent, MAPROFIX 563, was added to and mixed with the resulting mixture. The mentioned surfactant is a purified oral grade of sodium lauryl sulfate. The weight percent of the respective ingredients in the composition of this Example are listed below:

| Ingredient | % by Weight |
| --- | --- |
| Polyethylene glycol 8,000 (Carbowax ® 8,000) | 10.33 |
| Polyethylene glycol 400 (Carbowax ® 400) | 56.75 |
| Calcium peroxide (FMC grade - 60% CaO$_2$) | 4.54 |
| NaHCO$_3$, fine grade #3 | 27.24 |
| Surfactant - sodium lauryl sulfate (Maprofix 563 - Onyx-Chemical Co. | 1.14 |

Flavoring agents (e.g., 0.5% by weight) may be added to this composition to enhance palatability.

This toothpaste (or "gel") is a cosmetically acceptable dentifrice which produces bactericidally active oxygen in use. When 1g of this composition was dispersed and substantially dissolved in about 15g of water — deemed to approximately correspond to use in the mouth — a pH of 9.0 was measured. The composition is "package stable" (as generally recognized) under reasonable conditions of storage when packaged in a squeeze tube or pump-type of container; i.e. the formation of gases (CO$_2$ and O$_2$) that would otherwise occur in a single phase unstabilized composition of peroxide and bicarbonate is effectively inhibited. Typical test procedures for confirming such package stability involves subjecting the composition in a closed container to sustained storage at elevated temperatures. Samples of the composition of this Example were found to be stable for at least 2½ months, when subjected to such storage at 120° F. and at 105° F. The packages thus tested exhibited no perceptible swelling, and the product taken from the container showed available peroxide when subjected to testing in a potassium iodide solution.

| Ingredient | % by Weight |
| --- | --- |
| Polyethylene glycol 8,000 (Carbowax ® 8,000) | 9.3 |
| Polyethylene glycol 400 (Carbowax ® 400) | 51.0 |
| Calcium peroxide (FMC grade - 60% to CaO$_2$ | 4.1 |
| Baking Soda (Church & Dwight) Grade 3, | 24.6 |
| Calcium carbonate | 10.0 |
| Surfactant foaming agent - sodium lauryl sulfate | 1.0 |

The calcium carbonate in this composition serves as a dental abrasive (as does to some extent the NaHCO$_3$. Other dentally acceptable abrasives, such as 1 to 15% of dicalcium phosphate, can be used. Once again small quantities of flavoring agents can be added if desired. When 1g of this composition was dispersed and substantially dissolved in 15g of water as in Example I, the pH was again measured at 9.0. The final composition is again a package stable, cosmetically acceptable dentifrice which produces bactericidally active oxygen in use. The composition of this Example displayed the same excellent stability and continued peroxide activity after 2½ months storage at 105° and at 120° F., as the samples of Example I.

The flavoring agents can include known dentifrice adjuvants, such as mint flavor and other dentifrice flavors, methyl salicilate, menthol, sodium sacharin (or other sweeteners, e.g. Nutrisweet ®). Also, other conventional dentifrice components such as dentifrice abrasives, fluorine-containing compounds, colorants, etc. can be provided.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

We claim:

1. A non-aqueous peridontal paste or gel dentifrice composition, comprising:

a water soluble, non-aqueous vehicle having dispersed therein sodium bicarbonate or potassium bicarbonate and calcium peroxide without barrier coatings as the essential active agents providing bactericidal active oxygen upon breakdown of the peroxide by tissue contact and by reaction with the bicarbonate in the oral cavity, effective to thereby inhibit the motility of harmful anaerobic gum disease-causing bacteria that live and thrive therein in the gum crevices and which cannot survive in an oxygenated environment; said composition being substantially completely anhydrous; the quantities and relative proportions of said peroxide and bicarbonate being sufficient to provide quantities of bactericidally active oxygen upon breakdown of said peroxide by reaction with said bicarbonate upon intermixing with water and use in the oral cavity, and to provide a neutral or basic pH upon dispersal of said composition in water; the bicarbonate being present in a weight ratio of sodium bicarbonate to said peroxide in the range of 4:1 to 8:1, (or equivalent potassium bicarbonate), said peroxide comprising at least about 1% to about 10% by weight of the composition, where said peroxide content is calculated on the basis of 60% $CaO_2$; said bicarbonate having an average particle size from about 100 to about 2,000 microns, the stability of the peroxide being increased by decreasing the surface area of the bicarbonate by increasing its particle size; said water soluble non-aqueous vehicle being essentially hydrophilic, water soluble and adapted to rapidly dissolve with water when used, and having an effective viscosity for use as a toothpaste or gel between about 2,000 to 200,000 cps.

2. A composition in accordance with claim 1, wherein said bicarbonate is sodium bicarbonate; the weight ratio of said bicarbonate to said peroxide being in the range of 4:1 to 8:1, where said peroxide content is calculated on the basis of 60% $CaO_2$.

3. A composition in accordance with claim 2, wherein said weight ratio of bicarbonate to peroxide is in the range of 4:1 to 6:1, and said peroxide is present as from 4 to 6% by weight of said composition.

4. A composition in accordance with claim 3, which when dispersed in water provides a pH in the range of 7.0 to 9.5.

5. A composition in accordance with any of claims 1, 2, 3, or 4, further including an auxiliary stabilizer for further inhibiting decomposition of said peroxide and premature reaction between said peroxide and bicarbonate.

6. A composition in accordance with any of claim 1, 2, 3, or 4 further including from 1 to 7½% by weight of colloidal silica, for absorbing trace water in said composition to further stabilize same, and for acting as a thickener for said composition.

7. A composition in accordance with any of claims 1, 2, 3, or 4, further including from 1 to 15% by weight of dicalcium phosphate, as a dental abrasive.

8. A composition in accordance with any of claims 1, 2, 3, or 4, further including from 0.25 to 5.0% by weight of a foaming agent.

* * * * *